US005449145A

United States Patent [19]

Wortrich

[11] Patent Number: 5,449,145

[45] Date of Patent: Sep. 12, 1995

[54] VALVE DEVICE FOR CONTROLLING FLOWS IN SURGICAL APPLICATIONS

[75] Inventor: Theodore S. Wortrich, Long Beach, Calif.

[73] Assignee: Surgin Surgical Instrumentation, Inc., Tustin, Calif.

[21] Appl. No.: 134,410

[22] Filed: Oct. 8, 1993

[51] Int. Cl.$^6$ .................................................. F16K 3/26

[52] U.S. Cl. .................................... 251/322; 251/323; 251/325; 604/33; 604/249

[58] Field of Search ............... 251/322, 323, 324, 325; 604/33, 249

[56] References Cited

U.S. PATENT DOCUMENTS 2,669,233 2/1954 Friend .
2,940,465 6/1960 Frantz .
3,678,959 7/1972 Liposky .
4,456,223 6/1984 Ebling ............................... 604/33 X
4,548,197 10/1985 Kinoshita .
4,552,130 11/1985 Kinoshita .
4,696,305 9/1987 Von Berg ....................... 604/249 X
4,925,450 5/1990 Imonti et al. .
5,064,168 11/1991 Raines et al. ................... 251/324 X
5,125,910 6/1992 Freitas ................................ 604/249
5,188,591 2/1993 Dorsey, III .
5,228,646 7/1993 Raines ............................ 251/324 X
5,303,735 4/1994 Cerola et al. ..................... 137/596.2
5,312,373 5/1994 Freitas ................................ 604/249

*Primary Examiner*—Gerald A. Michalsky
*Attorney, Agent, or Firm*—Merchant, Gould, Smith, Edell, Welter & Schmidt

[57] ABSTRACT

A disposable trumpet valve for controlling irrigation and aspiration flows under manual operation comprises a conduit and a pair of spaced apart valve barrels of substantially greater cross-sectional size within which valve members are reciprocable under manual control. Large diameter sections of the valve barrels lead to transition wells merging in the same plane into the conduit and directing the flow path between a side port in the valve barrel and the bottom section of the barrel. Thus a large cross-sectional flow area is provided throughout in a device which may be manipulated with either hand. Integral seals on a slider piston function to block flow and prevent leakage, while at the same time substantial cost advantages are obtained.

8 Claims, 3 Drawing Sheets

VALVE DEVICE FOR CONTROLLING FLOWS IN SURGICAL APPLICATIONS

BACKGROUND OF THE INVENTION

This invention relates to low cost valve devices, and more particularly to manually operated valve systems for controlling irrigation and aspiration flows to surgical sites.

In surgical applications, most notably in laparoscopic and endoscopic procedures, it is preferred to utilize disposable elements for at least certain ones of the surgical instruments, rather than subjecting patients to the potential dangers of cross-contamination from prior users due to inadequate sterilization. This conclusion applies not only to simple surgical instruments, but to more complex instruments which may be used to provide dynamic functions during the duration of a surgery. For example, it is often desired to irrigate an operative site with a sterile solution and then to withdraw or aspirate fluid under suction. The aspirated fluid may include not only an irrigation solution, but also blood and other fluids, tissue and fragments. A number of procedures use an elongated probe and control flows into and out of the operative site by an externally operated valve device that is conveniently manipulated by the surgeon. This type of valve device has been used for many years, but earlier units were primarily expensive, complex designs that were intended to be reusable. Further, since the probes were fixed to the valve structure, the surgeon was afforded little opportunity to use the instrument in a variety of operating modes, or manipulate it readily in different positions.

More recently, workers in the field have devised disposable manual valve systems for use in surgical applications, these usually being called "trumpet valves" because key members on the top of two adjacent and parallel valve barrels can be selectively depressed by the surgeon against compression springs. An example of such a type of system is U.S. Pat. No. 5,064,168 to Raines et al. (assigned to Burron Medical, Inc.) in which an offset base portion of the valve is configured together with a valve barrel and an interior movable member for flow control. However, this design has interior corners and has not been found suitable for a number of modern laparoscopic and endoscopic procedures, in which it is critical to avoid restrictions and distortions in the flow path. If the aspirated flow does encounter restrictions, tissue or particulate might clog the instrument, a consequence which is to be avoided if at all possible.

The patent to Dorsey, U.S. Pat. No. 5,188,591 describes a trumpet valve which is intended to have certain operating advantages for irrigation control, based upon a bilaterally symmetrical arrangement of two valve chambers with respect to a transverse common conduit at one side, with ports extending radially outwardly from the other side in an orthogonal direction. The common conduit is in communication with each of the valve chambers through side orifices, so that a probe can be attached to either end of the common conduit. Because the irrigation and aspiration conduits couple into the opposite side of the chambers from the common conduit, this arrangement can be used by a right-handed surgeon with the probe extending from one end of the common conduit, or by a left-handed surgeon if the probe is reversed to the opposite end of the common conduit. However, the internal flow paths are restricted in size, because of the necessity of coupling into and out of side conduits, and because the geometry requires a number of O-ring seals and the use of biasing springs in the bottom of the chamber.

SUMMARY OF THE INVENTION

A valve configuration in accordance with the invention utilizes a valve barrel of substantially larger size than a base fluid conduit to which it is transversely coupled. Between the central portion of the barrel, which includes a side port for an incoming or outgoing fluid, and the end of the barrel which couples to the conduit, is a wide flow path including an interior transition well that merges into an open section of the conduit. In the intermediate region of the barrel is a reduced diameter section within which a cylindrical slider piston is reciprocable, the slider piston having an elongated transverse bore for communication between the port and the transition well. The slider piston is of an elastomeric material and includes circumferential seal rings at each end of its length, such that when the slider piston is in the non-actuated position, the port is sealed off from the transition well. When the slider piston is moved to the actuated position, however, the elongated bore extends into the transition region and provides an open communication path along the central axis of the barrel and through each side of the bore.

In accordance with other features, this valve arrangement includes a manually operable key member inserted into the open end of the valve barrel, coupled to the slider piston interior to the valve barrel, and mechanically biased toward the unactuated position by a spring disposed between the upper end of the valve barrel and the inner upper end of the key member. For ease of assembly, the upper end of the valve barrel has a reduced diameter neck portion and an uppermost circumferential flange against which inner projections on a cylindrical skirt of the key member engage to limit upward movement of the key member. Further, the valve may be constructed of several readily molded parts, which are fitted together and joined in such manner as to enable different support means to be fabricated.

The invention also comprises an improved trumpet valve, manufactured as a disposable, for irrigation/aspiration functions in surgical systems. In this configuration, two valve barrels are disposed in spaced apart, upstanding relation, along a common conduit. Each valve barrel and slider piston arrangement is as previously described, but the radial ports in the intermediate regions of the valve barrel bodies are disposed along the common plane of the two valve barrels, or at a slight angle outwardly. A support pad or surface on the underside of the conduit fits between the thumb and forefinger of a surgeon, whether used in the left hand or the right hand, and the key members can then be actuated with two fingertips in convenient fashion.

Another aspect of the invention is that the trumpet valve arrangement can be utilized with an attachable probe coupled to an output port of the conduit with a conventional threaded male/female connection or with an axial quick disconnect coupling. The opposite end of the conduit is typically closed, as with a luer fitting, but can be opened so that an operative element can be extended through the conduit and the probe into the operative site for other purposes, such as cauterizing. Further, the base unit, including the conduit and the transition wells, is conveniently molded as a separate piece with any one of several different support pads being attachable, through the use of different mold cavities in association with the basic mold, which can be closed off if no support pad is to be attached.

BRIEF DESCRIPTION OF THE DRAWINGS

A better understanding of the invention may be had by the reference to the following description, in conjunction with the accompanying drawings, in which.

DETAILED DESCRIPTION OF THE INVENTION

Figure 4:
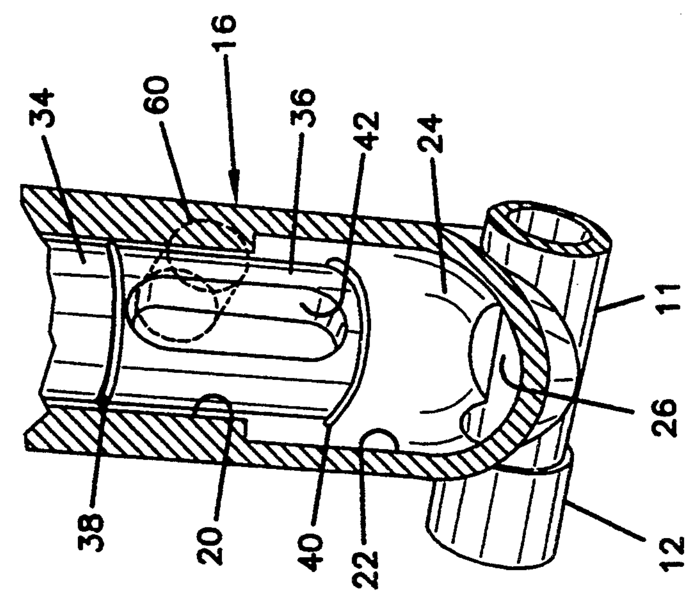
FIG. 4 is a fragmentary perspective view, partially broken away, of a single valve device as utilized in the arrangement of FIGS. 1–3, showing the slider piston in actuated position.

A valve device 10 in accordance with the invention is shown in FIGS. 1–4, to which reference is now made. A length of conduit 11 is disposed along a given linear axis, defining a conduit path of a predetermined internal diameter. The conduit 11 has an open port 12 at one end, the port 12 being interiorly threaded to receive a probe 13 which extends in a direction toward a surgical site, this direction predetermining the relationship of other elements in the system, as is described below. The opposite end port 14 also includes an interior thread, and in this example, is closed off with a luer closure 15. First and second valve barrels, 16 and 17 respectively, are coupled to the conduit 11 at spaced apart regions along its length, the valve barrels 16, 17 having central axes lying in a common plane and normal to the central axis of the conduit 11. As seen in the Figures, the barrels 16, 17 will typically be used in an upstanding relationship relative to the conduit 11, so that relative terms such as vertical, upper and lower are utilized for clarity of description, although it will be appreciated that in operation the device can be angled in different attitudes and ways depending on the circumstances.

Figure 1:
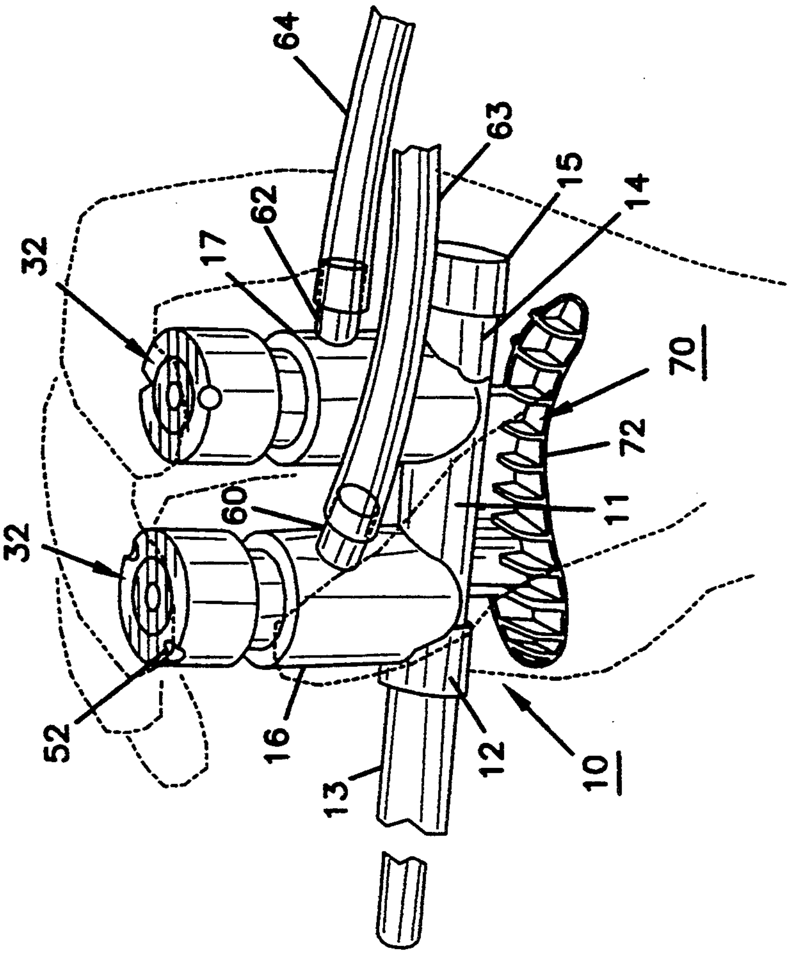
FIG. 1 is a perspective view of a typical operative usage of a valve device in accordance with the invention, as employed with an attached probe.
Figure 3:
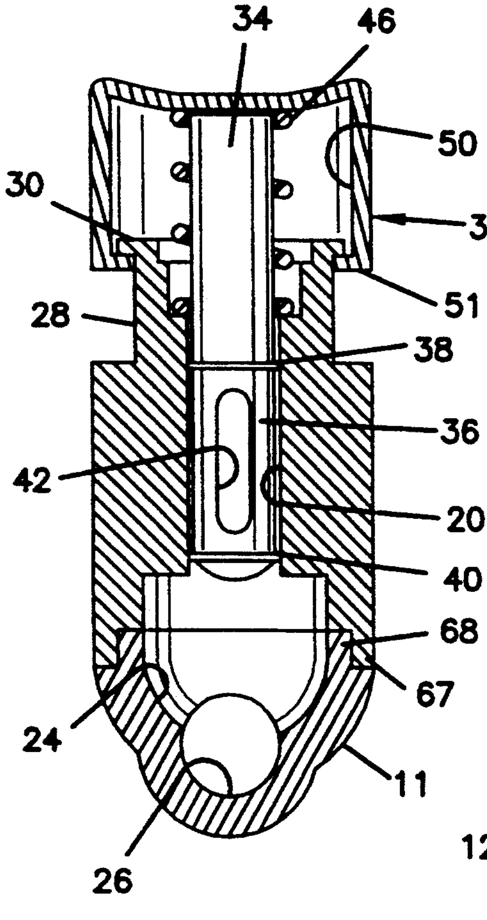
FIG. 3 is a side sectional view of the device of FIG. 2, showing a single valve barrel and slider piston.
Figure 2:
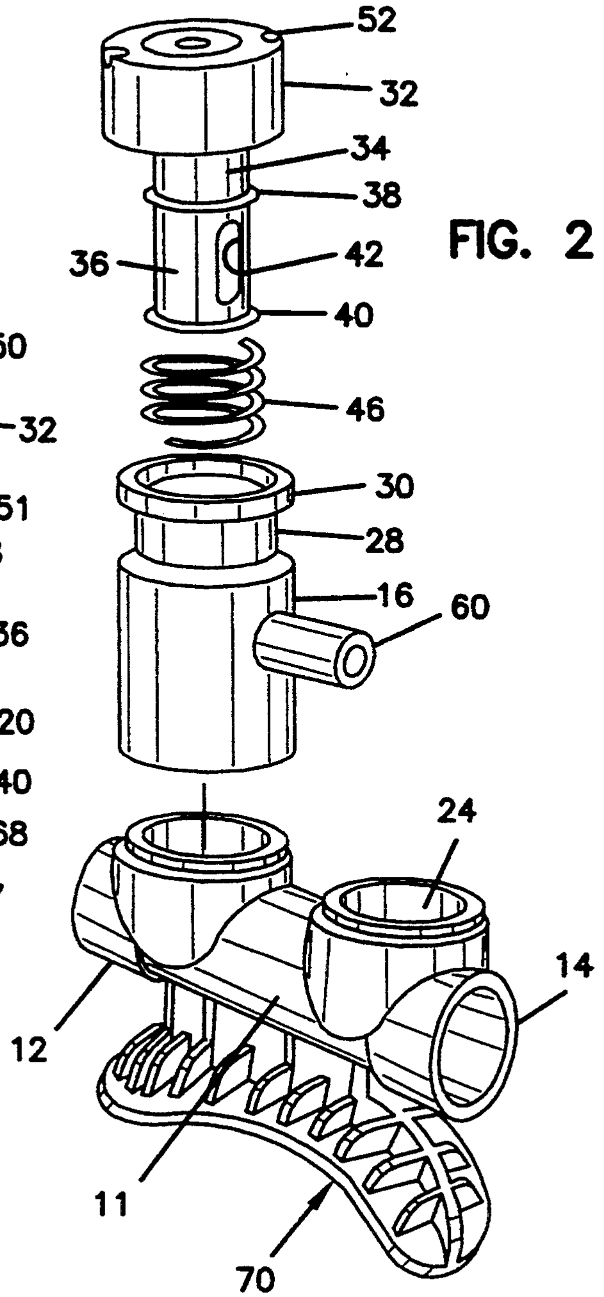
FIG. 2 is an exploded view of a portion of the valve device of FIG. 1.

The barrels 16, 17 are alike except for the geometrical relationship of a side port, as is described in greater detail below, and consequently a description of only one of the devices suffices to cover both. As seen particularly in FIGS. 2–4, the first barrel 16 includes a principal length of an outer diameter section that is substantially greater than the conduit 11. Along this principal length, the upper section 28 is of reduced inner diameter 20 and is then stepped outwardly to a larger diameter section 22 in the lower region. The larger diameter section merges into a transition well 24 at the bottom, converging smoothly into the lower half section of the inner conduit 26. At the upper end of the barrel 16, the inner diameter is larger, but the barrel also includes an upper section of reduced outer diameter 28 terminating in an uppermost circumferential flange 30. A key member 32 disposed above this upper section 28 has a slightly concave top surface for finger operation, as viewed in FIGS. 1 and 3. As best seen in FIGS. 2 and 3, the key member 32 includes a central shaft disposed along the central axis of the barrel 16, and extending downwardly into the reduced inner diameter of section 20. Depending from the key member shaft 34 is an elastomeric slider piston 36 of predetermined length and diameter.

At the upper end of the slider piston 36 is an integral circumferential seal ring 38 that, when the key member 32 is in the non-actuated position of FIG. 3, is above a side port, described below, in the barrel. The lower end of the slider piston 36 also includes an integral circumferential seal ring 40 which, as seen in FIG. 3 also is in the reduced inner diameter section 20 in this position. Between the two seal rings 38, 40 is an elongated interior bore 42, whose length and position are selected relative to a side port shown in dotted lines in FIGS. 3 and 4. Because the side port of the first valve barrel 16 must clear the second valve barrel, the side port is at a slight area to the common plane, as best seen in FIG. 1, so that the interior bore 42 is also at a slight angle to the common plane, as seen in FIGS. 3 and 4. When the key member 32 is depressed to the actuated position, the elongated interior bore 42 still is fully open to the side port, but the lower end of the bore 42 extends down into the larger diameter section 22 of the barrel, providing a flow path in both directions of substantial cross-sectional area relative to the conduit 11 cross-sectional area, as seen in FIG. 4. The key member 32 is biased toward the non-actuated position by a helical compression spring 46 about the key member shaft 34, and extending between the upper region of the barrel 16 and the under side of the top surface of the key member 32. The key member 32 also includes a depending cylindrical skirt or flange 50 that has, at its lower edge, two or more inwardly projected tabs 51 which snap over the outer edge of the circumferential flange 30 on the barrel 16, to thereafter define the upper limit of the non-actuated position. Vent apertures 52 in the upper surface of the key member 32 permit air passage to provide free reciprocal movement of the key member 32 without air compression effects.

The aspiration port 60, seen only in dotted lines in FIGS. 3 and 4, is at a slight acute angle to the common plane to provide clearance relative to the second barrel 17. The irrigation port 62 coupled to the second barrel 17 then lies in the common plane, the aspiration and irrigation lines 63, 64 are coupled to the ports 60, 62 respectively, and thereby directed away from the surgical site. As seen in FIG. 1, the surgeon's hand fits around a support pad 70 having a concave undersurface 72, with the surgeon's fingers separately fitting over the key members 32 on the two barrels 16, 17. Although the right hand of an operator is shown, it will be appreciated that the arrangement is symmetrical and that a left-handed operator can use it just as well.

For ease of manufacture, the barrels are made separately from the conduit 11 but the joinder line is disposed at the upper end of the transition wells 24, so that the entire support pad 70 and conduit 11, including end ports 12, 14 and transition wells 24 for both barrels, are molded as a single piece, as seen in FIGS. 2 and 3. Interlocking lips 67, 68 on the barrel 16 and transition section 24 enable easy assembly, using adhesive or bonding material (not shown).

In the operation of the system of FIGS. 1–4, the surgeon holds the device 10 in one hand, in the position indicated in FIG. 1, with finger control over both key members 32, and with the base support pads 70 resting in the web between thumb and the palm of the hand. Flows of sterile irrigation fluid in the line 64 and suction in the aspiration line 63 are constantly maintained, as the surgeon places the operative end of the probe 13 at the surgical site, as in laparoscopic or endoscopic surgery. He then simply depresses the appropriate key member 32, placing the key in the actuated position, as seen in FIG. 4, with incoming or outgoing flow finding a large cross-sectional area path between the port and the conduit. Since there is a double flow through both sides of the elongated bore 42, and the transition well 24 and larger diameter 22 of the barrels 16 or 17 provide unrestricted communication paths, any tissue, viscous or particulate matter flows freely and there is no tendency to clog the line. The circumferential seals 38, 40 at the opposite ends of the slider piston 36 permit movement without significant frictional restraint, but at the same time provide an effective sealing action at much lower cost than conventional O-rings.

Figure 5:
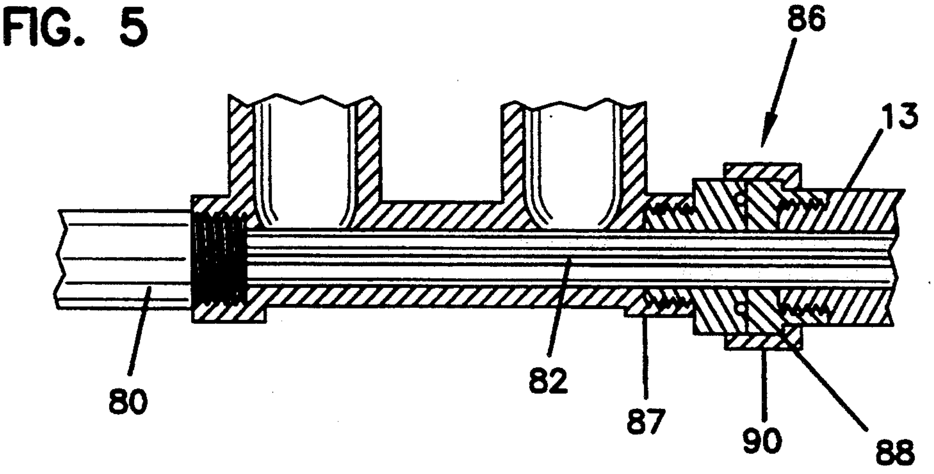
FIG. 5 is a side sectional fragmentary view of a portion of a valve device as in FIGS. 1–4, showing an added instrument coupled through the conduit and the probe.

A different application of the system is depicted in the side sectional view of FIG. 5, wherein the closed end port 14 on the side opposite the surgical site is opened, and used as a fitting for an additional instrument 80, such as a cauterizing needle 82 which can be extended through the conduit 11 and the probe 13 for use concurrently with the probe. This is a conventional operation with probe systems, and facilitated by the compact, versatile nature of the device. At the first port 12, another feature is shown, in that half 87 of a quick disconnect device 86 is threaded into the first port 12, and the opposite half 88 is threaded to the probe 13. The quick disconnect device 86 is a typical commercial unit, made in two halves 87, 88 each separately threaded into the receiving portion of the port 12 or the probe 13, but snapping together within a common structure 90 that includes O-rings and biasing springs. The quick disconnect connector is not shown in detail, but must be of a type that incorporates an adequate central bore for receiving the inserted element, here the cauterizing needle 82.

Figure 6:
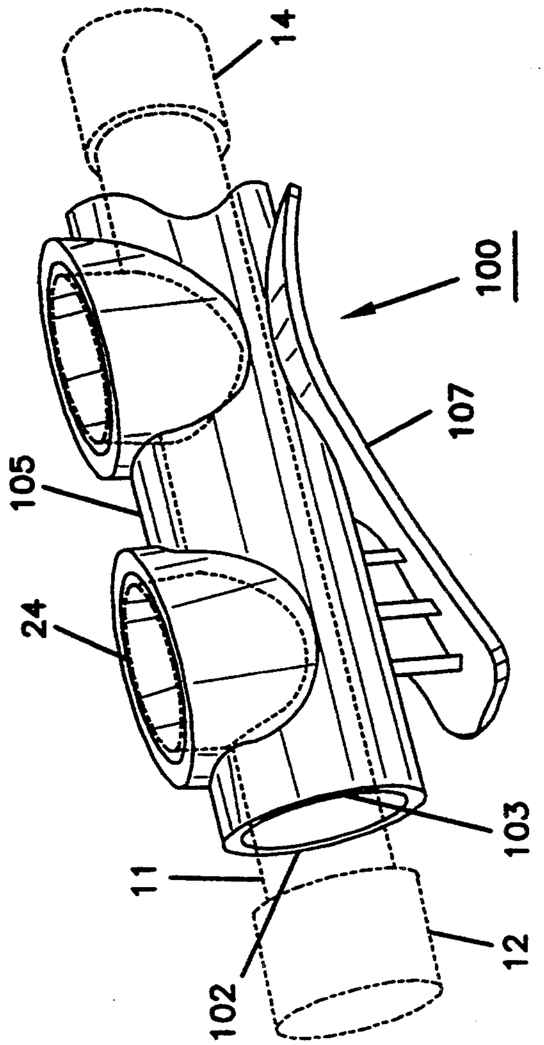
FIG. 6 is a perspective view of a first type of alternate support pad.

FIG. 6 depicts a different type of support pad structure in which the transition cells 24 and conduit 11 are molded as a single piece, without an integral support pad 70. This is done simply by closing off the mold to form a uniform conduit 11 on the underside, as seen in dotted lines in FIG. 6. Then two halves of a clamshell type or overlying unit 100 are snapped together about the molded conduit 11, as seen in FIG. 6. The two halves 102,103 may be adhesively joined or include internal self locking edges (not shown) at the joinder line 105. A support pad 107 is molded into the bottom of the unit 100 to provide a different support configuration that may be preferred by a particular user. This arrangement permits the base to be molded as a single unit, but to serve after modification when molding as a universal base for any of a variety of exterior clamshell-type supports. These optional supports can be larger, of special shapes for a unique need or ergonomic design, or incorporate other functional elements, such as controls, or useful attachments.

Although there have been described above and illustrated in the drawings various forms and modifications, it will be appreciated that the invention is not limited thereto but includes all variants and alternative forms within the scope of the appended claims.

I claim:

1. A low cost disposable valve comprising:

a cylindrical conduit forming a first port;

a valve barrel having a portion of greater inner wall diameter than the conduit coupled to and extending from the conduit, the barrel in the coupling region comprising an interior concavely curved transition well merging with the conduit, the barrel including an open terminal portion on the end opposite the conduit including interior valve barrel wall means for receiving a piston means therein;

side port means coupled to an intermediate region of the barrel spaced apart from the transition well therein;

piston means disposed within the interior valve barrel wall, the piston means comprising an elastomeric slider element of predetermined length having integral and spaced apart end seals for engagement with the interior valve barrel wall, the slider element also including a transverse elongated bore extending therethrough between the end seals and within the interior valve barrel wall, and the length of the piston means being such that the lower seal ring extends into the transition well of the barrel when the slider element is in the actuated position, the length and position of the elongated bore in the slider element providing a communication path through the elongated bore between the port and the opposite sides within the transition well when the slider element is in said actuated position; and means for mechanically biasing the piston means in the direction toward the non-actuated position.

2. A device as set forth in claim 1 above, wherein the piston means comprises an uppermost key member that is manually actuable, wherein the interior valve barrel wall includes a portion adjacent to and merging with the transition well that is substantially larger in diameter than the conduit, and a reduced diameter interior section receiving the piston means at a spaced apart region from the conduit, and wherein the means for biasing comprises a compression spring disposed between the upper region of the valve barrel at the reduced diameter interior section, and a surface of the key member.

3. A device as set forth in claim 2 above, wherein the valve barrel further includes a reduced outer diameter upper neck portion and a circumferential terminal flange extending radially outwardly therefrom, and wherein the key member includes a top actuating surface and a depending cylindrical skirt having interior lock means for engaging over the circumferential flange and limiting movement of the key member in the non-actuated direction, and wherein the conduit lies along a first selected axis and the valve barrel lies along a second selected axis that is perpendicular to and intersects the first.

4. A valve for communicating with a conduit of a given aperture size lying along a first axis comprising:

a valve body having an inner opening and lying along a second axis perpendicular to and intersecting the first axis, the valve body having a lower portion proximate the conduit including a merger section of larger inner size than the conduit aperture joining with the conduit, and an upper portion having an inner wall of smaller inner size than the inner section, the upper section including a port to be in communication with the conduit, and a valve piston disposed within the upper section of the valve body and spanning the port, the piston including a transverse bore and seal means, and being movable downwardly to an actuated position in which the lower portion of the piston extends into the lower portion of the valve body wherein the transverse bore provides a communication path between the port and the conduit.

5. A valve as set forth in claim 4 above, wherein the valve body lower portion comprises a curved lower part merging into a side of the conduit, and a straight sided upper part of fixed inner size, wherein the seal means of the valve piston includes seals both above and below the port, with the transverse bore therebetween, such that the communication path between the port and the conduit is established without criticality as to the angular position of the port about the second axis.

6. A valve as set forth in claim 4 above, wherein the valve body lower portion comprises a curved lower part merging into a side of the conduit extending along the first axis, and a straight sided upper part of fixed inner size, wherein the valve piston includes seals both above and below the port in the nonactuated position of the piston, with the lower section of the piston having a smaller external size than the inner wall of the valve body, with a portion of the seal means being in the merger section of the valve body when the valve piston is in the actuated position.

7. A valve for communicating with a conduit of a given inner aperture size lying along a first axis comprising:

a valve body having an inner opening lying about a second axis perpendicular to and intersecting the first axis, the valve body having a lower portion proximate the conduit including a merger section partially of larger inner size than the conduit aperture merging into the side of the conduit, and an upper portion having an inner wall of smaller inner size than the merger section, the upper portion including a port to be in communication with the conduit, and a valve piston including an upper and a lower section, disposed within the upper portion of the valve body and spanning the port, the piston including means defining, with the inner wall of the upper portion of the valve body, a channel along a lower section of the piston, the piston including seal means positioned along the lower section to seal off the channel within the inner wall when the piston is in a non-actuated position, and the piston being movable between the non-actuated position and an actuated position with the lower portion of the piston extending into the lower portion of the valve body, wherein the means defining a channel provides a communication path between the port and the conduit.

8. A valve for communicating with a conduit of a given inner aperture size lying along a first axis comprising:

a valve body having an inner opening lying about a second axis perpendicular to and intersecting the first axis, the valve body having a lower portion proximate the conduit including a merger section partially of larger inner size than the conduit aperture merging into the side of the conduit, the lower portion further comprising a curved lower part merging into a side of the conduit extending along the first axis, and a straight upper part of fixed inner size, and an upper portion having an inner wall of smaller inner size than the merger section, the upper portion including a port to be in communication with the conduit, and a valve piston including an upper and a lower section, disposed within the upper portion of the valve body and spanning the port, the lower section of the piston having a smaller external size than the inner wall of the valve body, the lower section of the piston and the inner wall of the upper portion of the valve body, defining a channel along a lower section of the piston, the piston including seal means positioned along the lower section to seal off the channel within the inner wall at points above and below the port, when the piston is in a non-actuated position, the piston being movable between the non-actuated position and an actuated position with the lower portion of the piston extending into the lower portion of the valve body, such that a portion of the seal means is in the merger section of the valve body and the means defining a channel provides a communication path between the port and the conduit.

* * * * *